United States Patent
Singh et al.

(10) Patent No.: US 7,537,910 B2
(45) Date of Patent: May 26, 2009

(54) LACTAMASE AMPLIFICATION SUBSTRATE

(75) Inventors: Rajendra Singh, San Jose, CA (US); Tabassum Naqvi, Fremont, CA (US)

(73) Assignee: Discoverx Corp., Fremont, CA (US)

( * ) Notice: Subject to any disclaimer, the term of this patent is extended or adjusted under 35 U.S.C. 154(b) by 324 days.

(21) Appl. No.: 11/449,414

(22) Filed: Jun. 8, 2006

(65) Prior Publication Data
US 2006/0292656 A1 Dec. 28, 2006

Related U.S. Application Data

(60) Provisional application No. 60/693,822, filed on Jun. 23, 2005.

(51) Int. Cl.
*C12Q 1/54* (2006.01)
(52) U.S. Cl. ........................... 435/14; 435/32
(58) Field of Classification Search ............ 435/14, 435/18, 32
See application file for complete search history.

(56) References Cited

U.S. PATENT DOCUMENTS

2003/0219848 A1 * 11/2003 Naqvi et al. .................. 435/18

OTHER PUBLICATIONS

Campbell R. Realization of beta-lactamase as a Versatile Fluorogenic Reporter. Trends in Biotechnology 22(5)208-211, May 2004.*
Micetich R. et al. Beta-Lactamases and Their Inhibitors: An Update. Current Medicinal Chemistry—AntiInfective Agents 1(3)193-213, 2002.*
Tabassum Naqvi, et al., "b Galactosidase Enzyme Fragment Complementation as a High Throughput Screening Protease Technology," *J of Biomolecular Screening*, 2004, vol. 9, No. 5 398-408.

* cited by examiner

*Primary Examiner*—Ralph Gitomer (57) ABSTRACT

An amplifiable β-lactamase substrate is provided comprising an enzyme donor fragment of β-galactosidase linked to form a ring to a β-lactam ring that is a substrate for lactamase and upon opening of the β-lactam ring the enzyme donor fragment becomes linearized. The cyclic substrate only weakly binds to the enzyme acceptor fragment of β-galactosidase. The substrate finds application for the sensitive detection of β-lactamase for direct detection of the enzyme or when the enzyme is used as a label.

12 Claims, 5 Drawing Sheets

LACTAMASE AMPLIFICATION SUBSTRATE

CROSS-REFERENCE TO RELATED APPLICATIONS

This application claims priority from U.S. Provisional Patent Application No. 60/693,822 filed on Jun. 23, 2005, which is hereby incorporated by reference in its entirety.

STATEMENT OF GOVERNMENTAL SUPPORT

None.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of detecting enzymatic reactions, and, more particularly, to the field of substrates for lactamase and their use.

2. Related Art

BACKGROUND

Assaying for lactamase has been of interest for a long time in determining its presence in prokaryotes as an indication of the prokaryotic resistance to penicillins and cephalosporins. A number of substrates have been developed for this purpose that provided for a chromogenic or fluorescent readout. Subsequently, lactamase became of interest as a label for detection of a wide variety of targets, where the lactamase was conjugated to various binding compounds, such as antibodies, biotin, avidin, receptors, etc. Depending upon the target, numerous assay protocols were developed employing lactamase and its substrates. In addition, the use of fragments of lactamase has been reported in an protein fragment complementation assay to study protein-protein interactions as well as monitor HIV fusion into cells.

Lactamase as a label has many desirable characteristics. It is small, so that in fusions it is unlikely to interfere with the function of the protein to which it is fused. It is a monomer in contrast to β-galactosidase, which is a tetramer. It is not found in eukaryotic cells, so there is usually no endogenous background when studying eukaryotic cells. However, it has a relatively low turnover rate in comparison to β-galactosidase and has no available chemiluminescent substrate. Also, it has been used as a selection marker, which would preclude lactamase as a label.

In performing assays for the determination of a wide variety of targets, there are many criteria in the choice of protocol. Particularly, when one is interested in intracellular events, the ability to detect events occurring at low concentrations can be very important. Enzymes have been used as labels, since for a single event, the enzymes are able to translate the single event into a plurality of events, based on the turnover of substrate. Even with enzyme labels, one is limited by the turnover rate of the enzyme, the environmental effect on the turnover rate and the presence of partial inhibitors. Therefore, for many enzymes it is desirable to further amplify the result obtained initially with the enzyme label.

Using the small lactamase as a label, one can follow the expression of proteins, the pathways associated with the activation or inhibition of transcription and translation, the presence and absence of transcription factors, signal induction by binding of ligands to receptors, and the like. By having an assay that can detect small differences in response or low levels of a target, one can investigate biological processes that might otherwise go undetected.

Relevant Literature

The detection of lactamase and the use of lactamase as a label is described in a large number of patents: U.S. Pat. No. 4,978,613 "Beta-lactamase assay employing chromogenic precipitating substrates"; U.S. Pat. No. 5,338,843, "Fluorogenic and chromogenic β lactamase substrates"; U.S. Pat. No. 5,583,217, "Fluorogenic and β lactamase substrates"; U.S. Pat. No. 6,472,205 "Cytosolic forms for β lactamase and uses thereof"; U.S. Pat. No. 6,291,162, "Cytosolic forms of β-lactamase and uses thereof"; U.S. Pat. No. 6,031,094, "Beta-lactam substrates and uses thereof"; U.S. Pat. No. 5,955,604, "Substrates for β lactamase and uses thereof"; U.S. Pat. No. 5,741,657, "Fluorogenic substrates for β lactamase and methods of use"; U.S. Patent application no. 2003/0003526, "Beta-lactamase substrates having phenolic ethers"; European Publication No. 0817785, "Substrates for Beta-lactamase and uses thereof"; European Publication No. 0553741, "Fluorogenic and chromogenic betalactamase substrates"; and European Publication No. 1081495, "Quenchers for fluorescence assays."

Relevant to the use of β-galactosidase fragments, particularly in cyclic form are U.S. Pat. No. 5,976,857, "Cross-linked polypeptide fragments of β galactosidase;" U.S. Pat. No. 5,976,783, "Bis-maleimido cross-linking agents;" and U.S. Pat. No. 5,763,196, "Assays using cross-linked polypeptide fragments of β-galactosidase."

The use of enzyme donors and enzyme acceptors in enzyme complementation assays is described in U.S. Pat. No. 4,708,929, "Methods for protein binding enzyme complementation assays," U.S. Pat. No. 5,643,734, "Methods for protein binding enzyme complementation assays," and other patents.

SUMMARY OF THE INVENTION

According to certain aspects of the present invention, lactamase is detected in assays in conjunction with a cyclic compound comprising a β-galactosidase fragment linked on opposite sides of a lactamase substrate to form a ring compound, where upon cleavage of the lactam ring linearization results. Cellular assays are performed intracellularly with a cell permeable substrate or extracellularly by lysing the cells. The linearized β-galactosidase fragment is assayed with the other β-galactosidase fragment and an appropriate substrate providing a fluorescent or chemiluminescent product. Importantly, the lactamase can be used as a label fused to a protein target of interest.

DESCRIPTION OF THE SPECIFIC EMBODIMENTS

Sensitive methods are provided for detection of β-lactamase (hereinafter referred to as "lactamase") using a cyclic substrate having an N-terminal proximal fragment of β-galactosidase ("enzyme donor" or "ED") linked on opposite sides of a β-lactam to form a ring capable of being hydrolyzed by β-lactamase with resulting linearization of the ED.

In a concomitant or subsequent reaction, the method employs enzyme fragment complementation ("EFC"), where ED is capable of independent complexation with a larger fragment of β-galactosidase ("enzyme acceptor" or "EA") to form an active β-galactosidase enzyme. The cyclic substrate has a low affinity for EA resulting in minimal background. Upon linearization, the affinity of the linearized substrate for EA is greatly increased providing for an amplified signal using a detectable β-galactosidase substrate with low background.

The method employs conventional procedures for detection of lactamase. In most cases the assay will involve cells in which the lactamase is present. When the cyclic substrate is membrane permeable or the membrane is made permeable by isotonic shock or other means, the assay may be performed intracellularly, expressing EA in the cell and using a permeable β-galactosidase substrate providing a detectable product. Alternatively, one may lyse the cells and determine the available linearized substrate by adding EA and a detectable β-galactosidase substrate. Also, the lactamase or lactamase fusion protein could be secreted and subsequently analyzed in the supernatant. Cells are thus available for further manipulation.

The ED cyclic reagent comprises the enzyme donor peptide sequence, two linkers terminating in a reactive functional group, a β-lactam cross-linking agent comprising complementary reactive functional groups, where the β-lactam is capable of being a lactamase substrate with cleavage of the lactam group and linearization of the cyclic ED substrate. The effect of the ring is to substantially inhibit the binding of the enzyme acceptor ("EA") fragment to the ED in the ring to form an active β-galactosidase enzyme. By appropriate positioning of the linkers associated with the enzyme donor peptide sequence, the length of the linkers, and the selection of the complementary functional groups, the length of the β-lactam within prescribed limits being substantially a given, the activity of the cyclic ED substrate binding to the EA to form an active β-galactosidase enzyme can be substantially repressed. By providing for the β-lactam moiety being present in the cross-linking agent, substantial benefits are achieved in the synthesis, purification and reduction in background.

The number of atoms in the ring may be widely varied depending upon the size of the ED, the spacing of the linkers, whether at one or both of the termini or along the ED chain, the length of the linkers, the nature of the reactive functionalities and the length of the β-lactam moiety. Usually, the ring chain will have at least about 100 atoms (where cyclic groups in the ring will be counted along the shortest chain), usually at least about 120 atoms, more usually at least about 180 atoms, and generally not more than about 350 atoms, more usually not more than about 300 atoms, and frequently less than about 250 atoms. The atoms in the chain will be carbon, nitrogen, oxygen, sulfur and phosphorous, while other heteroatoms may be present in the molecule, such as halogen. The nature and size of the ring will provide the substantial repression of active binding of the EA to the cyclic ED substrate to produce β-galactosidase enzyme activity.

The ring has a number of permitted variables: the spacing between the linkers; the length of the linkers; the size of the functional groups; and the β-lactam moiety as a minimum, that may be increased as necessary or desirable. Since a polypeptide may assume a number of different conformations based on the degrees of freedom that the polypeptide has, depending on the size of the ring, the nature of the other entities involved with the formation of the ring, and the space between the linkers, the ED will be constrained to assume a conformation that has a low affinity for the EA to form an active enzyme. Therefore, there is great flexibility in the system, as one may choose different variables in relation to the minimum number of atoms in the bridge of the cross-linking agent to provide the desired constraints on the ED when in the cyclic form.

The linkers may be a bond or have at least one atom in the chain, generally being from 1 to 20, usually not more than 16 atoms, in the chain, and may be aliphatic, alicyclic, aromatic or heterocyclic or combinations thereof. The linker is measured by the number of atoms from the α-carbon atom bonded to the glycine residue in the amino acid chain of the ED. For example, where cysteine is the amino acid that provides the linker, the chain would be O atom, the one sulfur atom serving as the reactive functional group.

Figure 3:
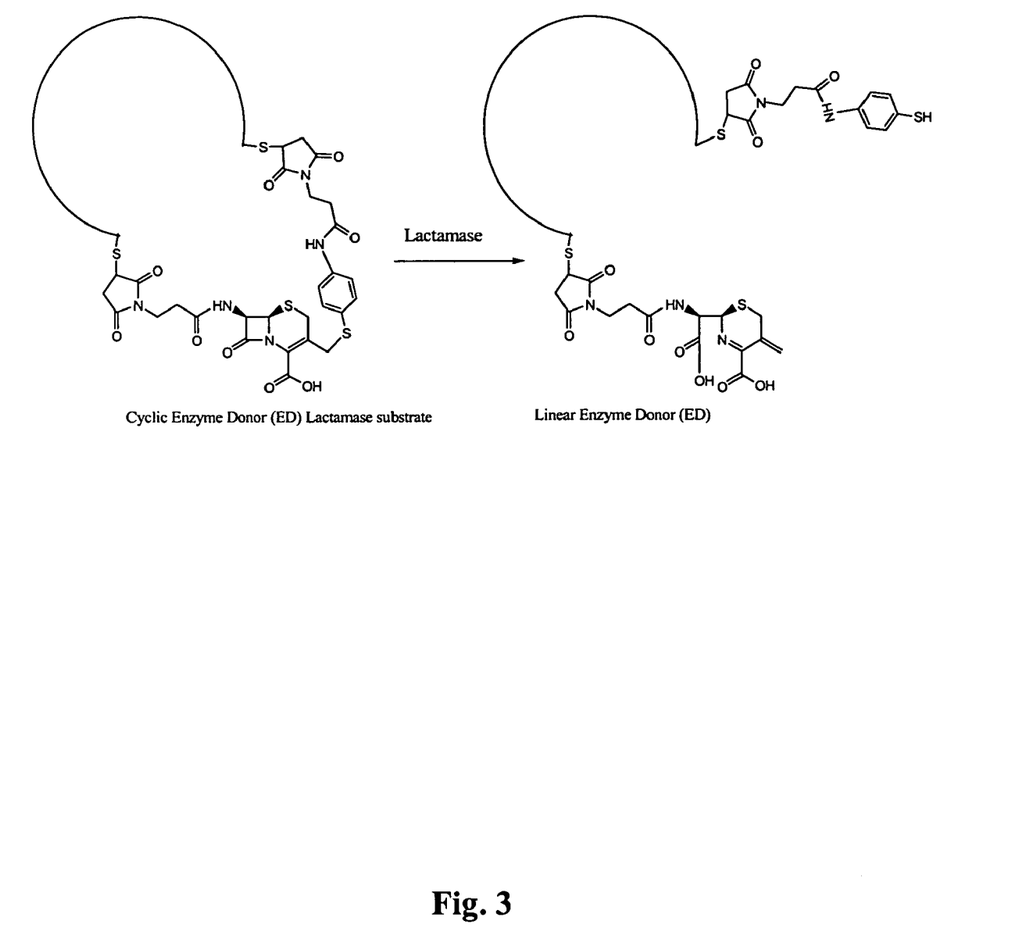
FIG. 3 is a reaction scheme (Scheme 3) showing the cleavage of a cyclized compound in the presence of a lactamase.

For the most part, the subject ED cyclic reagent will have the following formula:

wherein:

E D is the enzyme donor sequence having reactive functional groups extending from the sequence derived from N-proximal sequence of β-galactosidase, the functional groups usually being thio;

the two L's are the linking groups, which may be the same or different and are a bond or a linking group of from 1 to 20 atoms in the chain, usually from 1 to 16 atoms in the chain, may be aliphatic, alicyclic, aromatic, heterocyclic or combinations thereof, generally having other than hydrogen from 1 to 30, more usually from 1 to 20 atoms total, which are C, N, O, S, and P, usually including a combination of groups based on the functionality of BL to which the linking groups are bonded, wherein where cyclic groups are present the smaller number of atoms between the two bonds joining such ring to the adjacent members of the linking group are counted. The linking groups may include such functionalities as carbonyl groups, e.g., esters and amides, amines, thioethers, and may be saturated or unsaturated, including aromatic unsaturation; heterocycles;

the two F's are the same or different and are the functional groups resulting from the linking of the Fs to the β-lactam moiety, with the active functional groups forming the F's being compatible with the functionalities of the amino acids of the ED and the β-lactam moiety, where the F's may be formed from joining a mercaptan and an activated olefin, halide, pseudohalide, S-pyridyl, etc., amines and a N-hydroxy succinimide ester, imidate ester, isocyanate, isothiocyanate, activated halogen, etc., carboxyl and carbodiimide, hydrazide, etc. The resulting functional groups are thioethers, disulfides, amides, amidines, urea, thiourea, hydrazides, and the like;

BL is the β-lactam moiety. The β-lactam moiety will include the four membered heterocyclic β-lactam ring, which may be part of a penicillin, cephalosporin or other molecule that provides the necessary characteristics for the subject invention. Those characteristics are: being capable of being a cross-linking agent to form the cyclic ED substrate, being a lactamase substrate, and upon opening of the β-lactam ring (as shown by the ring opening in Scheme 3), resulting in the linearization of the ED cyclic reagent. Numerous substrates have been reported in the literature having these characteristics. See, for example, U.S. Pat. No. 5,741,657 to Tsien et al., "Fluorogenic substrates for β lactamase and methods of use;" U.S. Pat. No. 5,583,217 to Quante, et al. "Fluorogenic and chromogenic β-lactamase substrates;" and U.S. Pat. No. 4,965,193 to Chen, "Detection of microbial β lactamase" where the substrates can be adapted to be used in the ED substrate.

Besides the β-lactam moiety, there may be from about 0 to 4, more usually 0 to 3 other molecular entities, e.g., thiopyran, particularly fused, carboxyl, alkyl, etc., not counting the terminal groups that provide for the reactive functionality. Of particular interest is cephalosporin that has a substituted methyl group at the 3-position of the fused thiopyran ring, e.g., as present in the cephalosporin ring:

As can be seen, amine and keto groups are on the opposite side of the methyl.

The ED may have the minimum number of the β-galactosidase N-proximal sequence that provides sufficient activity when complexed with the EA to detect the lactamase produced in the assay. Of the N-proximal sequence, generally the ED will have at least 28 amino acids, more usually at least about 35 amino acids and not more than about 120 amino acids, more usually not more than about 90 amino acids and preferably not more than about 60 amino acids. The number of amino acids selected will depend upon the required assay sensitivity, the level of background under the conditions of the assay, ease of synthesis of the cyclic ED substrate and the ratio of background to signal that is obtained.

The cyclic ED substrate will generally provide less than 5%, usually less than about 1%, preferably less than about 0.1%, of the enzyme activity observed at the same concentration ratio, than is observed with the linearized cyclic ED substrate. Test concentrations of the cyclic ED substrate will generally be in the range of about 10 nM to 500 nM, with the concentration of the EA generally being in the range of about 5-100 times the concentration of the cyclic ED substrate.

The β-lactam moiety will usually have a fused second ring and be substituted at the 3-position in the case of cephalosporin, an ethylenic carbon atom, by an α-substituted methyl group, with a substituent capable of leaving the methyl group, whereby when the β-lactam is opened, the substituent will be released with formation of an exo-olefin. The release of the substituent results in the linearization of the cyclic ED substrate. Various substituents may be used that allow for release, particularly groups that support a negative charge, such as thio groups, oxy groups, and amino groups, which groups may be of some complexity, e.g., thiophenol, pyridinium, nitrophenol, thionitrobenzoic acid, quinone methide, etc.

Since the β-lactam moiety normally has two different functionalities for attachment, namely an amino group and an active α-methyl substituent, as shown above, the linkers will generally not be symmetrical. For the amino group, one may use various acid groups to form amides or reductive amination with an aldehyde. For the side chain, various strategies may be used. The functionalized α-methyl group at the 3-position of the six-membered ring can be displaced with a variety of functionalities. For example, halo may be displaced with thio, oxy or amino. Where an hydroxyl group is present, it may be esterified or etherified with a group that enhances displacement, such as a substituted difluoracetyl group, a substituted arylsulfonate, polyhalobenzyl, alkylsulfonates, or could be converted to iodides or pyridinium derivatives etc.

Groups that can be used for cyclization of a polypeptide are extensively described in Davies, 2003, J. of Peptide Science 9, 471-501, which article is specifically incorporated herein by reference.

In the cyclization step, one may use homogeneous or heterogeneous conditions, primarily homogeneous. In the homogeneous cyclization, normally inverse addition is employed, where one of the reactants is added to the other reactant, so that one reactant is in very high concentration as compared to the other reactant. Generally, the di-functionalized lactam will be added to the ED. For heterogeneous synthesis, one of the functionalities of the lactam compound or the polypeptide is bound to a functionalized surface, followed by addition of the other reactant. After completion of reaction, the resulting product is cleaved from the surface and cyclization caused with appropriate reagents. By proper choice of conditions, cleavage from the surface may be slow, so that polymerization of the cleaved product is minimized. In either system, the cyclized product is separated from the linear product, either as monomer or oligomer, and the cyclized product isolated at least substantially free of the linear product.

The particular method employed in the subject invention has a number of advantages in allowing for the isolation of a substantially pure product free of linear contaminant. The functionalized ED is combined with the cross-linking agent under mild conditions and under conditions of relatively high dilution to enhance the formation of the monomer. Desirably, the functionalities employed are sulfhydryl groups present in cysteine, which can be readily introduced into the ED at or proximal to the termini of the ED by synthesis or recombinant expression. Desirably, the lactam unit will be added to a dilute solution of the functionalized ED. That is, the ED that is employed will have already been modified so as to have two reactive groups that are complementary to the reactive groups of lactam unit. For such pairs of groups, please see U.S. Pat. No. 5,976,857 and references cited therein. The lactam moiety will also be modified to provide for the linking groups to react with the ED functionalities.

The functionalized ED will be in an appropriately buffered medium, e.g., phosphate, acetate, MOPS, etc., at a pH in the range of about 5 to 8, usually 6 to 7.5. The concentration of the functionalized ED will be in the range of about 5-100 μM, more usually in the range of about 10 to 50 μM. The concentration of buffer will generally be sufficient to maintain the pH in the range of about 6-8 during the course of the reaction, generally being in the range of about 25-500 mM, more usually in the range of about 50-200 mM, the particular concentration above the indicated minimum not being significant. The ratio of the concentration of the lactam unit (including linkers) to the functionalized ED will generally be in the range of about 0.5-10:1, more usually in the range of about 1-5:1. An approximately equimolar amount of the functionalized lactam unit will be initially slowly added to the functionalized ED, generally being in the range of about 0.8-1.2:1, more usually in the range of about 0.9-1.1:1. The volume of the solution of lactam unit will vary depending upon the concentration and desired ratio of lactam unit to functionalized ED, generally being in the range of about 0.2-1:1 v/v, more usually in the range of about 0.25-0.75 v/v. Generally, the concentration of the lactam unit in the solution being added and the functionalized ED in its solution will be in the range of about 10 to 200 μM. The solution may be buffered as described above or may be water. While other inert polar solvents may be used for any of the solutions, aqueous solutions are preferred.

The addition of the lactam unit to the solution of functionalized ED will be slow, e.g., dropwise. Thus, at any time the volume of lactam unit added to the total volume of the reaction mixture will be less than about 0.1, usually less than about 0.01 v/v. The temperature will generally be moderate and may be room temperature, generally being in the range of about 10-50° C., more usually 15-30° C. The time for the addition and total reaction will vary widely with the size of the reaction mixture, the amount of active components, the temperature, the nature of the functional groups, and the like. Generally, after completion of the addition, there will be an incubation of from about 5 to 120 min, usually from about 10 to 60 mm, again varying with the factors indicated above. To ensure that there are substantially no remaining reactive groups present on the functionalized ED, a second aliquot of the lactam unit may be added in a manner similar to the addition of the first aliquot of the lactam unit. The course of the reaction may be monitored by any convenient analytical means to determine the amount of unreacted reactant(s) and/or product. HPLC, mass spectrometry, gas chromatography, or other rapid analytical method may be employed with advantage.

The product may be conveniently purified using RP-HPLC. Conventional eluents may be used, employing solutions, such as aqueous trifluoroacetic acid, trifluoroacetic acid/acetonitrile, formic acid or acetic acid/acetonitrile and trialkylammonium acetate in acetonitrile or water, etc.

It is understood that the concentrations and volumes indicated are for small preparations. Large commercial sized preparations would be scaled up and by using more sophisticated equipment could provide for higher concentrations of the reactants and more rapid additions.

The resulting product may then be used to determine lactamase activity in a sample. The conditions for the assay will vary depending upon whether the cyclic substrate and detectable substrate are determined intracellularly or extracellularly in a lysate. In both assays, cells are employed that express lactamase. For the intracellular assay, the cells also express EA and retain the EA in the cytosol or other compartment, as appropriate. After growing the cells in accordance with the purpose of the assay, the cyclic substrate and detectable β-galactosidase substrate are then introduced into the cells and the cells incubated. One or more readings may be taken by various means for determining the lactamase activity in the cell. For the extracellular assay, the cells need only express the lactamase. After growing the cells in accordance with the purpose of the assay, the cells may be lysed and the lactamase detected using the cyclic ED substrate, EA and detectable β-galactosidase substrate.

The sample may be derived from any source, where the production of lactamase is of interest. Lactamase has found extensive use as a label in assays. The use of lactamase is found in Galarneau, et al. 2002 Nature Biotechnology 20, 619-22; Campbell 2004 Trends in Biotechnology 22, 208-11; Wehrman, et al. 2002 PNAS USA 99, 3469-74; and Cavrois, et al. 2002 Nature Biotechnology 20, 1151-4; Moore, et al 1997 Analytical Biochemistry 247, 203-9, U.S. Pat. Nos. 5,338,843, 5,583,217, 5,955,604; and 6,031,094; U.S. Patent application no. 2003/0003526; EPA nos. 0 553 741; and 1 081 495, (all referenced above) whose disclosures as to applications for detection of lactamase are specifically incorporated herein by reference. The term "lactamase," as is understood in the art, refers to an enzyme which catalyses the opening and hydrolysis of the beta-lactam ring of beta-lactam antibiotics such as penicillins and cephalosporins. It also includes diverse sequences that contain D-alanyl-D-alanine carboxypeptidase B, aminopeptidase (DmpB), alkaline D-peptidase, animal D-Ala-D-Ala carboxypeptidase homologues and the class A and C beta-lactamases and eukaryotic beta-lactamase homologs which are variously described as: transesterases, non-ribosomal peptide synthetases and hypothetical proteins. Many are serine peptidases belonging to MEROPS peptidase family S12 (D-Ala-D-Ala carboxypeptidase B family, clan SE). The beta-lactamases are classified as S12 non-peptidase homologues; these either have been found experimentally to be without peptidase activity, or lack amino acid residues that are believed to be essential for the catalytic activity.

Thus, the subject compositions may be used for high throughput screening, where one is interested in the development of drugs. One may be interested in determining the lactamase activity in a physiological sample, such as blood, plasma, saliva, cerebrospinal fluid, bone marrow, biopsy, etc. Alternatively, one may be interested in the determination of lactamase activity in a culture, where one may employ a lysate. One may be interested in pathways involving expression of a protein, where the transcriptional regulatory region controls the expression of lactamase. Alternatively, one may be interested in translocation, where the translocation of a cellular component results in the formation of an active lactamase. In addition, one can use the subject substrate to identify lactamase-containing organisms, particularly infectious lactamase-containing organisms. The particular sample will be treated as is conventional for the nature of the sample and the subject assay.

The concentration of the cyclic ED substrate and the linearized ED substrate in the assay medium with EA will generally be in the range of about 0.1 to 1000 nM, more usually in the range of 2 to 500 nM. (It is understood that in referring to "linearized ED substrate" that this compound is no longer a substrate for lactamase and serves to complex with EA.) The concentration of the cyclic ED substrate with the lactamase will generally be in the range of about 0.5 nM to 1M, more usually in the range of about 10 to 500 nM. Where the assay is carried out in a single step rather than two steps involving first the cyclic ED substrate with the lactamase, followed by the addition of EA and substrate, the concentration of the cyclic ED substrate in the assay medium will generally be in the range indicated for the lactamase reaction.

As indicated the assay may be carried out in a single step or two steps, depending upon reagent compatibility and integration with high throughput instrumentation for reagent dispensing and readout. Two steps allow for modification of the assay medium in the second step, such as the addition of a different buffer, dilution of the cyclic ED substrate, reducing background, terminating the first enzymatic reaction, improving precision, etc. Incubation of the first step will usually be for at least about 60 min, and not more than 24 hrs. The particular time is selected to provide for sufficient linearization of the cyclic ED substrate to provide for a robust signal in the second step. Depending upon the particular protocol, the assay method may involve a single reading at a predetermined time, more than one reading, or the reaction may be followed kinetically. In a single step assay, one will usually follow the reaction kinetically, taking readings at different times.

The assay method of the invention is usually conducted in an assay medium comprising the desired reagents in a suitable buffer. The buffer formulation is generally not critical, but must not interfere with the linearization of the cyclic ED substrate. In general, any buffer compatible with complementation of β-galactosidase fragments is acceptable, including phosphate buffer, MOPS buffer and the like. Conveniently, the buffer has a concentration of about 100 mM to about 300 mM sodium phosphate, about 100 mM to about 500 mM sodium chloride, about 1 mM to about 6 mM magnesium chloride, about 5 mM to about 15 mM EGTA (ethylene glycol tetraacetic acid) or EDTA (ethylenediamine tetraacetic acid) and about 5 mM to about 200 mM sodium azide having a pH of about 6 to about 8. Of course, these components may be modified in relation to the nature of the sample.

A chelating agent can be added to any polypeptide or protein containing cysteine or methionine residues to protect against metal catalyzed oxidation. Addition of a stabilizing amount of chelating agent for metal ions (such as EDTA or EGTA) is desirable. A bactericide, such as sodium azide, can be present to prevent bacterial growth, especially during storage, biocides such as kathon (Rohm & Haas) can be used as a preservative.

Other materials can be present including but not limited to magnesium ions or other ions for enzyme activity, reagents to prevent degradation of cysteine residues such as dithiothreitol (DTT), solubilizing agents such as ethylene glycol, and non-ionic surfactants such as fatty acid condensation products of sorbitol and ethylene oxide, e.g., TWEEN 20 (® ICI Americas, Inc.), and the like. Methionine and bovine serum albumin (BSA) may also be present.

The storage stable assay medium is typically aqueous. The cyclic ED substrate is usually present at a concentration from about 2 pM to about 5 µM and enzyme acceptor is present in varying degrees of molar excess. The excess EA will be optimized to minimize background, depending upon the residual activity of the cyclic ED substrate. Therefore, generally the excess will not exceed 100-fold excess, usually not more than 10-50-fold excess, taking into consideration the turnover rate of the enzyme, the proportion of cleavage of the lactam unit to intact cyclic ED substrate, the residual activity of the cyclic ED substrate, the anticipated protease concentration range, and the like. While the cyclic ED substrate and EA may be stored together, they will generally be stored separately.

After combining the various ancillary components for the lactamase reaction, the sample, and the cyclic ED substrate to form a reaction mixture, the medium will usually be incubated. The temperature and duration of the incubation or incubations for a two-step process will be compatible with the ability of the lactamase to cleave the cyclic ED substrate, and the linearized cyclic ED substrate to perform in the β-galactosidase reaction. In some formats, additional assay components and incubations may be necessary. EA and β-galactosidase substrates may be added together or separately and complementation activity is measured.

A β-galactosidase substrate is used in the method of the invention that, when cleaved by β-galactosidase, results in a detectable change in the amount of light absorbance (optical density) or emission. That is, cleavage of the substrate results in the appearance or disappearance of a colored, chemiluminescent or fluorescent product suitable for spectrophotometric, chemiluminescent or fluorometric analysis. Substrates suitable for use with β-galactosidase include but are not limited to p-aminophenyl-β-D-galactopyranoside, 2'-N-(hexadecanol)-N-(amino-4'-nitrophenyl)-β-D-galactopyranoside, 4-methylumbelliferyl-β-D-galactopyranoside, naphthyl-A-S-B1-β-D-galactopyranoside, 2-naphthyl-A-S-B1-β-D-galactopyranoside monohydrate, o-naphthyl-β-D-galactopyranoside, p-naphthyl-β-D-galactopyranoside, phenyl-β-D-galactopyranoside, 5-bromo-4-chloro-3-indolyl-β-D-galactopyranoside, resorufin-β-D-galactopyranoside, 7-hydroxy-4-trifluoromethylcoumarin, omega-nitrostyryl-β-D-galactopyranoside, fluorescein-B-D-galactopyranoside, chlorophenol red β-galactoside and the like. Preferred substrates are chlorophenol red β-galactoside (CPRG) and o-nitrophenyl-β-D-galactoside (ONPG). Incubation with the enzyme substrate results in the cleavage of the substrate to produce a product that is detectable, preferably by color. In high throughput applications, chemiluminescence readout is preferred as it causes less interference. Galactosidase substrates derived from the adamantyl phenyl 1,2 dioxetanes (Applied Biosystems), acridan dioxetanes (Lumigen) or spiro tricyclotridecence phenyl 1,2 dioxetanes (Michigan Diagnostics) are the reagents of choice in these applications. For high signals, the BetaGlow reagent system from Promega can also be used.

Unless specified otherwise above, the relative amounts of reagents used in the invention can vary to provide for concentrations of the reagents which can substantially optimize the sensitivity of the assay method, since one will be considering the concentration range of the lactamase, the background resulting from the interaction of the cyclic ED substrate and the EA, the effect of components of the sample on the reaction, etc. The reagents can be provided as dry powders, usually lyophilized, including any excipients, which on dissolution will provide for a reagent solution having the appropriate concentration for performing the assay method of the invention.

Kits can be provided so that the appropriate reagents are available in a convenient format. The kits can include the cyclic ED substrate, EA, and β-galactosidase substrate, as well as buffer and other ancillary reagents, as well as cells having lactamase label expression constructs, EA expression constructs, and the like. Conveniently, the EA and substrate may be combined in the same container, also including buffer.

The following examples are offered by way of illustration and not by way of limitation.

EXPERIMENTAL

Synthesis and Characterization of Compounds 1, 2 & 3

Figure 1:
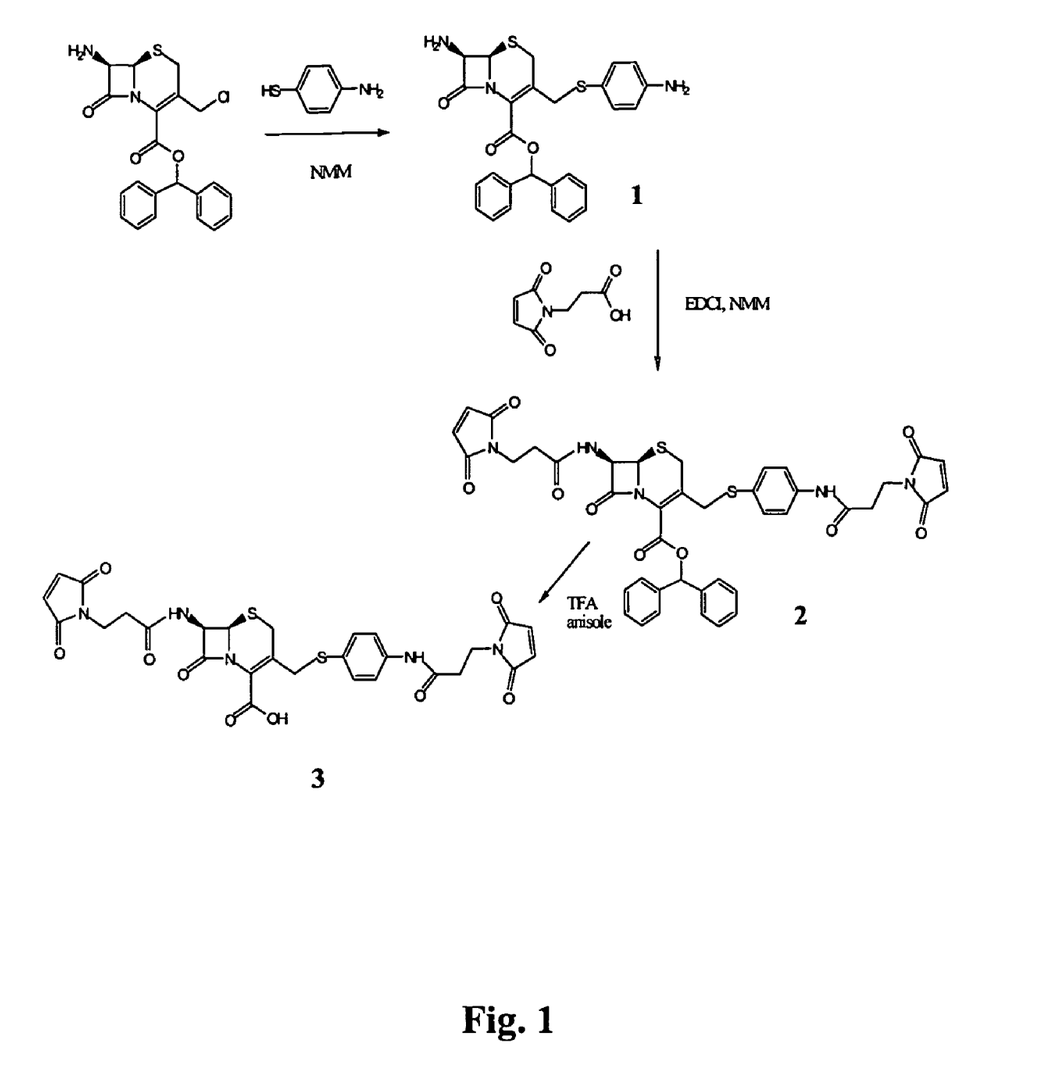
FIG. 1 is a reaction scheme (Scheme 1) showing synthesis of compounds 1, 2 and 3 in a synthesis of a lactam compound for cyclization to an enzyme donor (ED)
Figure 2:
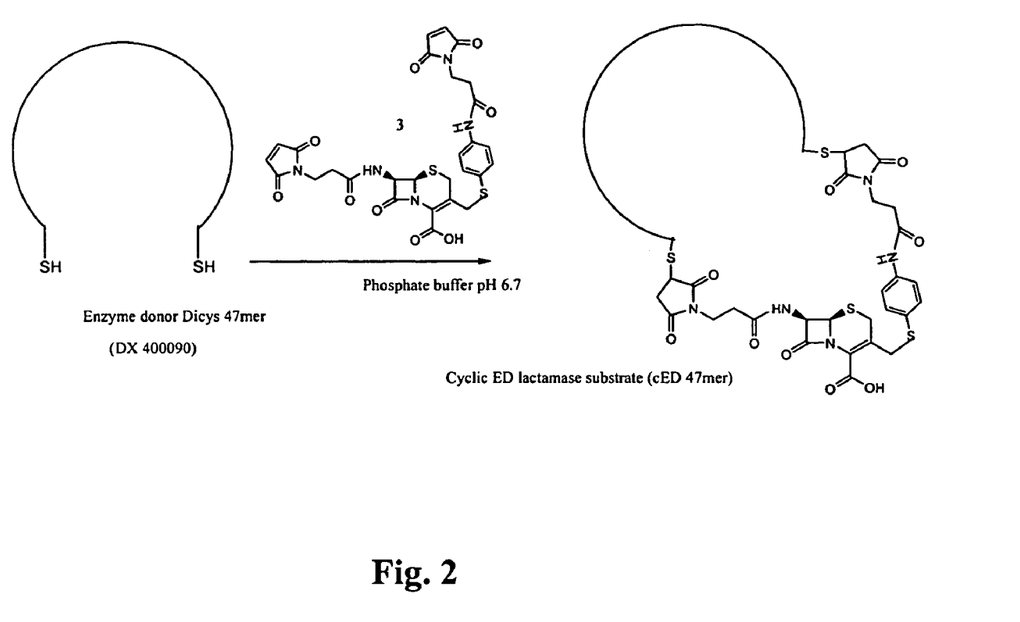
FIG. 2 is a reaction scheme (Scheme 2) showing cyclization of an ED with compound 3.

Scheme 1 (FIG. 1) represents the synthesis of a lactam structure (cephem derivative) 3 adapted for cyclization to ED, proceeding through intermediates 1 and 2. Scheme 2 (FIG. 2)

represents the cyclization of ED with cephem derivative 3. Scheme 3 (FIG. 3) represents the cleavage of the cyclic ED of FIG. 2 with lactamase to form linear ED having a cleaved lactam ring.

(Unless otherwise indicated all reagents were obtained from Sigma-Aldrich.)

Preparation of 1

ACLH. HCl (7 Amino-3-chloromethyl-3-Cephem-4-carboxylic acid diphenyl methyl ester hydrochloride (Otsuka Chemical, Japan, 500 mg, 1.1 mmole) was suspended in 10 ml DMF followed by N-methyl morpholine NMM (150 µl) to neutralize the HCl salt and get a clear solution. 4-aminothiophenol (150 mg, 1.5 mmole) was then added to the above solution and the reaction stirred at ambient temperature for 4-5 h. The reaction was monitored on TLC. The DMF was evaporated in vacuo and the concentrated oil was made into a slurry using silica gel (230-400 mesh). The slurry was purified by flash chromatography on a silica gel (230-400 mesh) using a MeOH/CH$_2$Cl$_2$ gradient of 2-15% to afford 315 mg (62.6%) of the title compound. $^1$H (400 MHz, DMSO-d6): δ 8.8 (s, 2H), 7.61-7.25 (m, 10H), 6.97 (d, J=8.6 Hz, 2H), 6.75 (s, 1H), 6.46 (d, J=8.6 Hz, 2H), 4.99 (d, J=5.2 Hz, 1H), 4.82 (d, J=4.80 Hz, 1H), 3.84 (d, J=12.8 Hz, 1H), 3.62 (d, J=13.6 Hz, 1H), 3.48 (d, J=17.6 Hz, 1H), 3.44 (d, J=10.0 Hz, 1H); ESI-MS: M+H 504 (Found); 503 (calc).

Preparation of 2

A solution of N— maleoyl-β-alanine (0.3 g, 1.78 mmole,) and 1-hydroxybenzotriazole (0.25 g, 1.78 mmole, 6 equiv.) in 1.5 ml of anhydrous DMF was cooled at 0° C. EDCI.HCl (0.34 g, 1.78 mmole,) freshly prepared in DMF (200 ul) and neutralized with NMM (100 ul) was then added. To this activated solution, 1 (150 mg, 0.298 mmole) in anhydrous DMF (1.5 ml) was added and the reaction mixture stirred at ambient temperature overnight. The solvent was evaporated in vacuo on a rotary evaporator and the residual oil suspended in water. The suspension was extracted with ethyl acetate (50 ml×3) and the organic phase washed with 5% w/v citric acid (10 ml×2), water (10 ml×2) and aqueous 5% w/v NaHCO$_3$ ((10 ml×2), brine (10 ml) and finally with water till neutral pH and dried over anhydrous sodium sulfate. The solvent was removed and the residual oil triturated with hexane to afford 260 mg (32.2%) of crude product. The crude product was subjected to flash silica gel column chromatography. The compound was eluted at 0-3% MeOH/CH$_2$Cl$_2$ solvent gradient to afford 170 mg (21%) of pure product 2. $^1$H (400 MHz, CDCl$_3$): 7.41-7.26 (m, 11H), 7.25 (d, J=8.8 Hz, 2H), 6.88 (s, 2H), 6.75 (s, 2H), 6.70 (d, J=8.4 Hz, 2H), 6.65 (s, 2H), 5.17 (d, J=4.0 Hz, 1H), 4.87 (d, J=4.0 Hz, 1H), 3.90 (d, J=18.4, 1H), 3.85 (m, 4H), 3.50 (d, J=17.6 Hz, 1H), 2.75 (m, 4H); ESI-MS: M+(Na+)=828 (Found); 805 (calc).

Preparation of 3

To a solution of 2 (6.7 mg, 0.0083 mmole) in 1 mL of anhydrous dichloromethane (CH$_2$Cl$_2$) was added m-cresol (50 µl) and trifluoroacetic acid (150 µL) with cooling (ice bath). The mixture was stirred for 1 h at while cooled in the ice bath, followed by the addition of anhydrous diethyl ether (1 mL). The precipitate was collected and washed with ether (1 mL×5) to afford 1.2 mg (90%) of 3 as a yellow colored powder. The purity of the compound was assessed by RP-HPLC. ESI-MS: M+640 (Found); 640 (Calc.). The linear ED compound 3 contains a lactam ring structure, linking groups and maleimide groups on either end.

Reduction of Linear ED

Linear ED compound 3 (5 mg, DiscoveRx, Fremont, Calif.) was dissolved in water (1 mL) and treated with DTT (5 mg) overnight at ambient conditions. It was then subjected to RP-HPLC purification employing 25% C-45% D (Buffer C=0.1% TFA/H2O; Buffer D=0.1% TFA/CH3CN) gradient in 25 min to afford pure 2.5 mg (50%) linear ED Ac-CSLAVVLQRRDWENPGVTQLNRLAAHPP-FASWRNSEEARTDCPSQQL (SEQ ID NO:1) (DX-400090) having free sulfhydryls. This was then immediately employed in the next step for cyclization. The above sequence is nearly identical to the N-terminal region of *E. coli* β galactosidase, Accession No. AAN78938, beginning at residue 7, with the addition of an N terminal cysteine and a cysteine replacement for arginine near the C terminus. Other regions of the known β galactosidase sequence may be adapted for use as the ED.

Cyclization of ED

Referring now to FIG. 2, to the above freshly purified ED 3 (4 mL, 65 µM), 100 mM sodium phosphate buffer pH 8.0 (1 mL) was added to adjust the pH between 6.7 to 7.0. To the buffer solution (1 mL), DMF (500 µL) was added to bring the volume up to 1.5 mL. To this solution an equimolar concentration of compound 3 in DMF (200 µl) was added drop-wise under vigorous stirring for 10 min The reaction was left at ambient conditions for 15 min and then a second aliquot of equimolar concentration of compound 3 was added for 10 min so as to ensure complete reaction with the sulfhydryls. The reaction mixture was left at ambient conditions for 3 h and then the progress of the reaction monitored by RP-HPLC. The cyclic ED lactamase substrate was purified to homogeneity by RP-HPLC employing 25% C-45% D (Buffer C=0.1% TFA/H2O; Buffer D=0.1% TFA/CH3CN) on a C18 column (Zorbax, Agilent). The fractions collected were lyophilized, resuspended in water and the concentration of the cyclic ED lactamase substrate assessed by UV-VIS spectroscopy at 280 nm ($\epsilon_{280}$=10000/M cm, ~15% unoptimized yield). The molecular weight of the cyclic ED was corroborated by ESI-MS: M+6031 (Found); 6031 (calc.).

Enzyme Fragment Complementation (EFC) Assay

Figure 4:
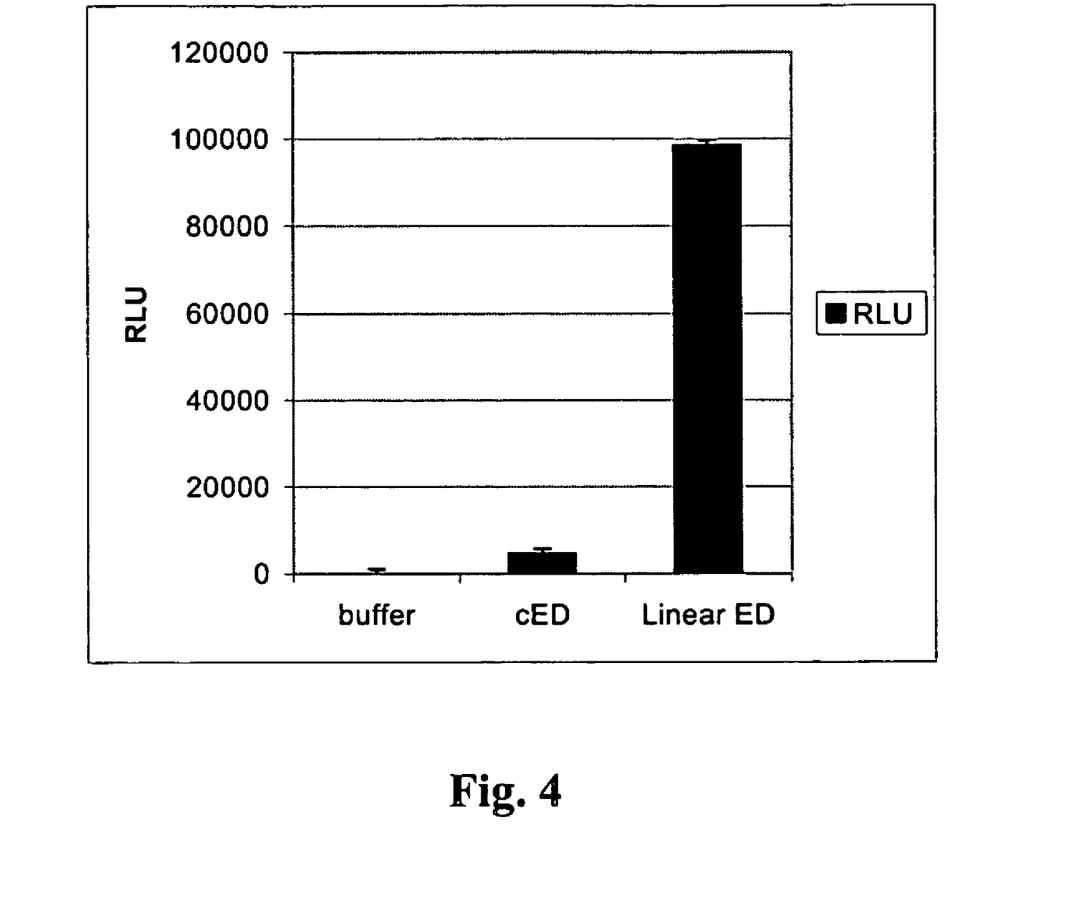
FIG. 4 is a bar graph of a comparison of the enzyme fragment complementation ("EFC") activity of the cyclic ED lactamase substrate and linear ED with EA.

For determination of EFC activity, 10 µL of 50 nM cyclic ED-Lactamase substrate (cED47mer) or 10 µl linear ED (Cysteines capped with maleimide, DiscoveRx, Fremont, Calif.) 50 nM was added to 20 µl EDDB Enzyme donor dilution buffer (MES 10 mM, NaCl 200 mM, EGTA 10 mM, BSA 2 mg/ml, NaN3 14.6 mM) (DiscoveRx, Fremont, Calif.) in a 384-well white plate. Subsequently, 10 µl EA (DiscoveRx, Fremont, Calif.) followed by 10 µl of chemiluminescence substrate (0.4 mM of Galacton Star™ and 2 mg/ml of Emerald II™ (Tropix) in EA core buffer (DiscoveRx, Fremont, Calif.) were added and further incubated at room temperature for 60 min. The signal was read on Lumicount (Packard) with an integration time of 1 s per well at PMT set up to 1100V. The bar graph of FIG. 4 represents the EFC activity for Cyclic-Lactamase ED (cED47mer, i.e., the compound produced in FIG. 2) and linear ED (Cysteines capped with maleimide, DiscoveRx, Fremont, Calif.). FIG. 4 shows a reduction of EFC activity for cyclic lactamase ED substrate compared to linear ED (cED 47mer).

Protocol for Lactamase Cleavage

The assay comprises two basic steps:
1) hydrolysis of the lactam in the cyclic ED lactamase substrate (cED 47mer) by the lactamase to yield a linear ED; and
2) detection of the linear ED by EA and β-galactosidase chemiluminescent substrate. The lactamase reaction step comprises 101 of cell lysate (<4000 CHOK1 cells, DiscoveRx, Fremont, Calif.) or cell lysis buffer (part #

30-175, DiscoveRx, Fremont, Calif.), 10 µl cED47mer substrate at 50 nM and 10 µl of lactamase (TEM-1, Invitrogen Part # PV3575) at varying concentrations. The reaction mixture is then incubated at ambient temperature for various time intervals. The detection step comprises addition of 10 µL1 EA (1-2 µM, DiscoveRx, Fremont, Calif.) and 10 µl chemiluminescent substrate reagent (Applied Biosystems, Foster City, Calif.).

Figure 5:
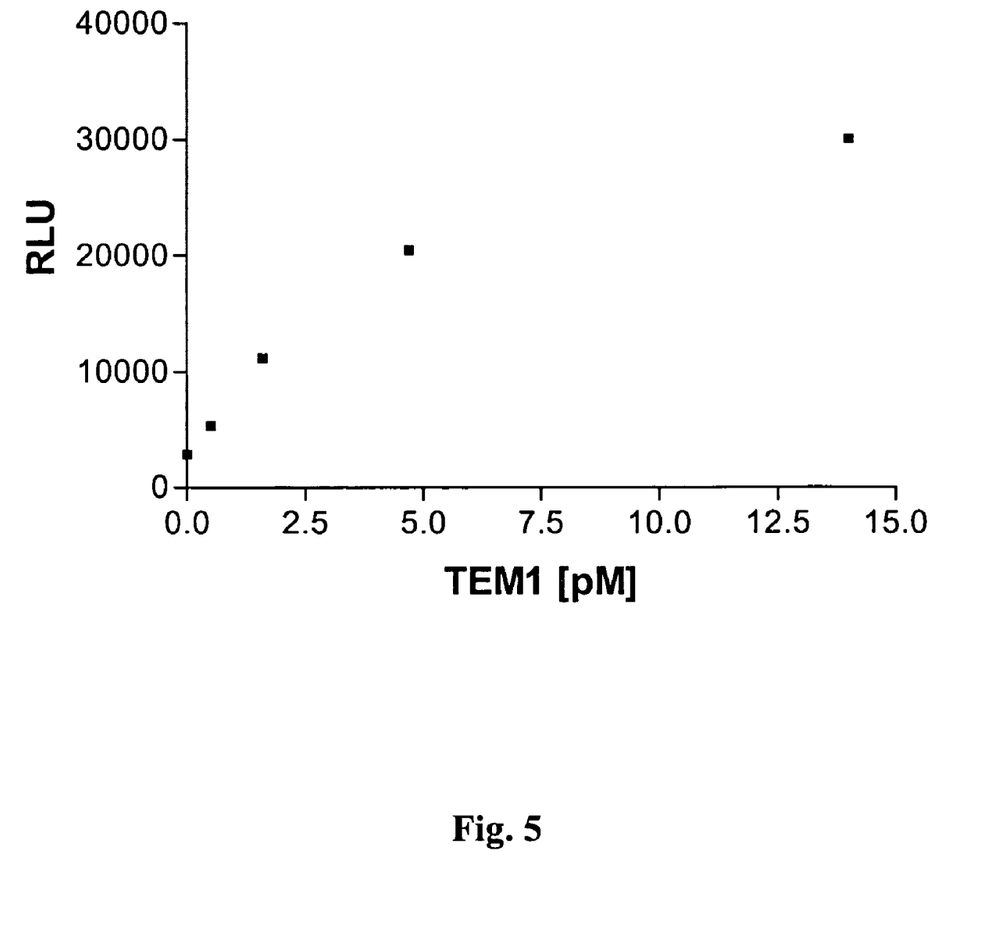
FIG. 5 is a graph of the activity of the ED β-lactamase linearized substrate with EA.

FIG. 5 represents the cleavage of Cyclic ED with lactamase enzyme at various concentrations for a 3-hour incubation in cell lysates. The chemiluminescence was read 1 hr after addition of EA and chemiluminescent substrate on a Packard Lumincount Reader (Packard Instruments, Meridien, Conn.) with the PMT set at 1100V and read time 1 second per well.

FIG. 5 shows that the sensitivity levels of spiked TEM1 lactamase detection in CHOK1 cell lysates in RLU (relative luminescence units) increased with concentration of *E. coli* TEM1 lactamase (picomole) in a dose dependent fashion.

It is evident from the above results that the subject invention provides for a significant enhancement in the detection of a wide variety of analytes of interest, employing as the detection scheme the production of an active lactamase detected with the cyclic ED substrate of the subject invention, EA and an appropriate β-galactosidase substrate, particularly a chemiluminescent substrate that is not available directly with lactamase. In addition, there is a substantial increase in sensitivity in the detection of lactamase, where there is an interest in the presence of lactamase, such as with infectious organisms.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cyclic lactamase substrate comprising an enzyme donor fragment of β-galactosidase joined on opposite sides of a β-lactam ring, wherein upon hydrolysis of said lactam ring, the activity of said enzyme donor fragment of β-galactosidase in complexing with the enzyme acceptor fragment of β-galactosidase is increased at least 10-fold.

2. A cyclic lactamase substrate according to claim 1, wherein said β-lactam ring is part of a cephalosporin molecule.

3. A cyclic lactamase substrate according to claim 2, wherein said enzyme donor fragment has a sequence of from 35 to 90 amino acids of said β-galactosidase.

4. A cyclic lactamase substrate according to claim 1, wherein said enzyme donor fragment includes a cysteine proximal to each terminus and is joined to said β-lactam ring through thio ethers.

5. A cyclic lactamase substrate of the formula:

wherein:

E D is an enzyme donor sequence of β-galactosidase having reactive functional groups extending from the sequence and not more than weakly capable of complexing with the enzyme acceptor fragment of β-galactosidase and capable of strongly complexing with the enzyme acceptor fragment of β-galactosidase upon linearization:

the two L's are the linking groups, which may be the same or different and are a bond or a linking group of from 1 to 20 atoms in the chain;

the two F's are the same or different and are the functional groups resulting from the linking of the Fs to the β-lactam moiety; and

SEQUENCE LISTING

```
<160> NUMBER OF SEQ ID NOS: 1

<210> SEQ ID NO 1
<211> LENGTH: 48
<212> TYPE: PRT
<213> ORGANISM: Artificial Sequence
<220> FEATURE:
<221> NAME/KEY: ACETYLATION
<223> OTHER INFORMATION: Description of Artificial Sequence: Synthetic
      ED construct

<400> SEQUENCE: 1

Cys Ser Leu Ala Val Val Leu Gln Gln Arg Arg Asp Trp Glu Asn
1               5                   10                  15

Pro Gly Val Thr Gln Leu Asn Arg Leu Ala Ala His Pro Pro Phe
                20                  25                  30

Ala Ser Trp Arg Asn Ser Glu Glu Ala Arg Thr Asp Cys Pro Ser
                35                  40                  45

Gln Gln Leu
```

BL is the β-lactam moiety
wherein upon cleavage of the β-lactam moiety, F is released resulting in linearization of the cyclic lactamase substrate.

6. A cyclic lactamase substrate according to claim 5, wherein said BL is a cephalosporin linked at the methylene group at the 3 position to F.

7. A cyclic lactamase substrate according to claim 5, wherein said Ls have individually at least one of a carbonyl group or thioether group.

8. A cyclic lactamase substrate of the formula:

wherein:
E D is an enzyme donor sequence of β-galactosidase having reactive functional groups extending from the sequence and not more than weakly capable of complexing with the enzyme acceptor fragment of β-galactosidase and capable of strongly complexing with the enzyme acceptor fragment of β-galactosidase upon linearization;
Ls are a bond or linking group of from 1 to 16 carbon atoms;
the two Fs are formed by joining to L through a mercaptan or amine; and
BL is the β-lactam moiety.

9. A cyclic lactamase substrate according to claim 8, wherein said Fs are linked through a mercaptan to an activated olefin, halide, pseudohalide, isothiocyanate, or S-pyridyl.

10. A cyclic lactamase substrate according to claim 9, wherein said Fs are linked through a mercaptan by the compound and BL is a cephalosporin moiety.

11. A cyclic lactamase substrate according to claim 10, wherein said Ls are a bond and said ED terminates with a cysteine at each terminus.

12. A cyclic lactamase substrate according to claim 8, wherein said Fs are linked through an amine to an N-hydroxy succinimide ester, imidate ester isocyanate, isothiocyanate, or activated halogen.

* * * * *

UNITED STATES PATENT AND TRADEMARK OFFICE
CERTIFICATE OF CORRECTION

PATENT NO. : 7,537,910 B2
APPLICATION NO. : 11/449414
DATED : May 26, 2009
INVENTOR(S) : Rajendra Singh It is certified that error appears in the above-identified patent and that said Letters Patent is hereby corrected as shown below:

At Col. 16, line 40, a comma is missing.

Claim #12 should read as follows:

12. A cyclic lactamase substrate according to claim 13, wherein said Fs are linked through an amine to an N-hydroxy succinimide ester, imidate ester, isocyanate, isothiocyanate, or activated halogen.

Signed and Sealed this

Thirtieth Day of June, 2009

JOHN DOLL
*Acting Director of the United States Patent and Trademark Office*